United States Patent
Wang et al.

[11] Patent Number: 5,869,734
[45] Date of Patent: Feb. 9, 1999

[54] PREPARATION OF OPTICALLY ACTIVE (S)-(–) AND (R)-(+)-DEOXYSPERGUALIN AND NOVEL INTERMEDIATES THEREOF

[75] Inventors: Xuebao Wang, East Brunswick; John K. Thottathil, Princeton, both of N.J.

[73] Assignee: Bristol-Myers Squibb Co., Princeton, N.J.

[21] Appl. No.: 715,175

[22] Filed: Sep. 23, 1996

Related U.S. Application Data

[60] Provisional application No. 60/004,341, Sep. 26, 1995.
[51] Int. Cl.$^6$ .................................................. C07C 279/24
[52] U.S. Cl. .......................... 560/25; 562/434; 568/139
[58] Field of Search ................................ 560/25; 562/434

[56] References Cited

U.S. PATENT DOCUMENTS

| | | | |
|---|---|---|---|
| 4,518,532 | 5/1985 | Umezawa et al. | 260/404.5 |
| 4,518,802 | 5/1985 | Umezawa et al. | 564/201 |
| 4,525,299 | 6/1985 | Umezawa et al. | 260/112.5 |
| 4,710,517 | 12/1987 | Umezawa et al. | 514/616 |
| 4,851,446 | 7/1989 | Umezawa et al. | 514/620 |
| 4,876,244 | 10/1989 | Umezawa et al. | 514/19 |
| 4,983,328 | 1/1991 | Umezawa et al. | 260/404.5 |
| 5,002,756 | 3/1991 | Nemoto et al. | 424/10 |
| 5,162,581 | 11/1992 | Ikai et al. | 564/157 |
| 5,196,453 | 3/1993 | Umeda et al. | 514/614 |

FOREIGN PATENT DOCUMENTS

| | | |
|---|---|---|
| 1 187 513 | 5/1985 | Canada . |
| 1 263 316 | 11/1989 | Canada . |

OTHER PUBLICATIONS

Umeda, The Journal of Antibiotics vol. XL (9) 1316, Sep. 1987.

Fluka Catalog Chiral Compounds Chemistry p. 149, 1995.

Iwasawa et al., "Synthesis of (–)–15–Deoxyspergualin and (–)–Spergualin–15–Phosphate", *Journal of Antibiotics*, vol. 12, pp. 1665–1669.

*Primary Examiner*—Robert Gerstl
*Attorney, Agent, or Firm*—Prabodh I. Almaula

[57] ABSTRACT

A process for preparing optically active (S)-(–) and (R)-(+)-deoxyspergualin and salts thereof of the formula I

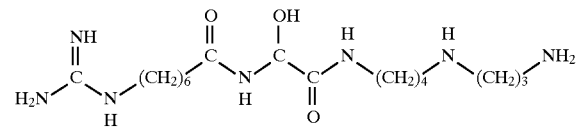

by reacting a compound of formula II

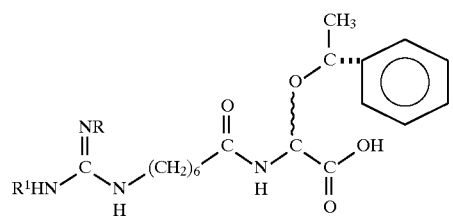

with a compound of formula III

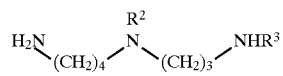

in the presence of a condensing/dehydrating agent and an organic or inorganic base in an organic solvent to form a compound of formula IV

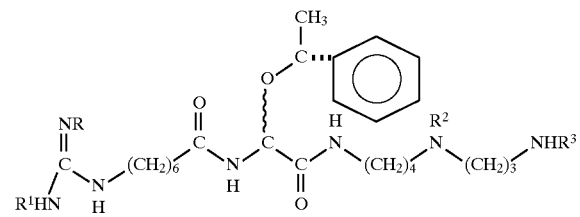

which can then be converted to the desired final product of formula I via deprotection and hydrogenolysis. The invention also comprises the compounds of the formula II, IV and VII

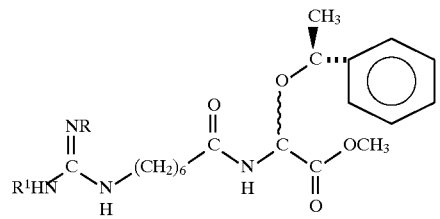

8 Claims, No Drawings

PREPARATION OF OPTICALLY ACTIVE (S)-(−) AND (R)-(+)-DEOXYSPERGUALIN AND NOVEL INTERMEDIATES THEREOF

This application claims the benefit of provisional application Ser. No. 60/004,341, filed Sep. 26, 1995.

BRIEF DESCRIPTION OF THE INVENTION

In accordance with the present invention, a novel process is disclosed for preparing deoxyspergualin and salts thereof represented by the following formula

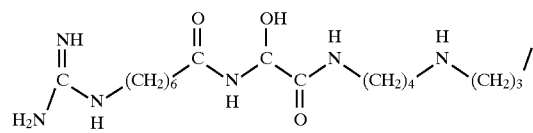

and the name N-[4-(3-aminopropyl)aminobutyl]-2-(w-guanidinofatty acid amido)-2-substituted-ethanamides. Compounds of formula I are disclosed in U.S. Pat. Nos. 4,518,532, 4,525,299 and 5,162,581 (incorporated by reference herein). Compounds of the formula I can exist as the optically active (S)-(−) and (R)-(+)-deoxyspergualin represented by formula

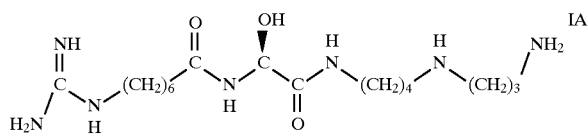

and

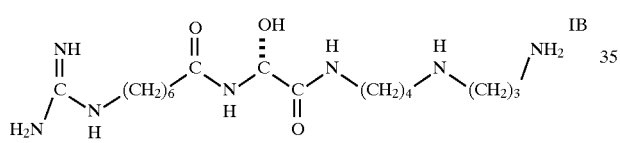

respectively. The invention also includes novel intermediates used to prepare compounds of formula I, IA and IB.

The compounds of formula I, IA and IB have antitumor and various other biological and pharmacological activity.

DETAILED DESCRIPTION OF THE INVENTION

The present novel process can be carried out by reacting a compound of formula

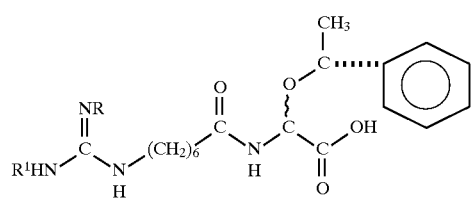

where R and $R^1$ are nitrogen protecting groups such as benzyloxycarbonyl or t-butoxycarbonyl (BOC), with a compound of formula

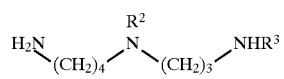

where $R^2$ and $R^3$ are nitrogen protecting groups such as benzyloxycarbonyl or BOC in the presence of a condensing/dehydrating agent such as propyl phosphonic acid anhydride and an organic or inorganic base such as triethylamine (TEA), 1,5-diazabicyclo[4.3.0]non-5-ene (DBN), or diisopropylethylamine (DIPEA), etc., in an organic solvent such as methylene chloride, toluene, tetrahydrofuran, etc. to form the novel compounds of formula

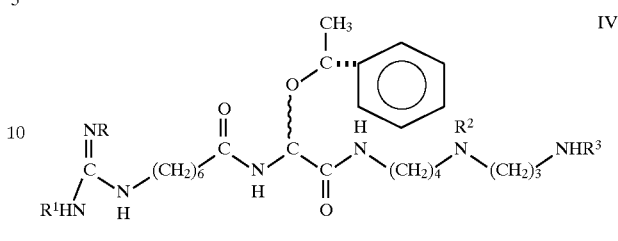

Compounds of formula IV can then be converted to the desired final product of formula I via deprotection and hydrogenolysis as known by those of ordinary skill in the art.

Compounds of formula II are novel intermediates and are mixtures of diastereomers as represented by IIA and IIB:

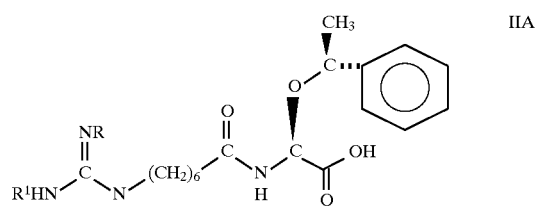

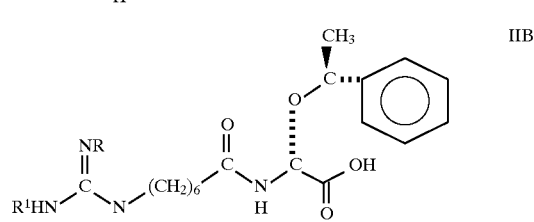

Compounds of formula IIA and IIB can be separated at this point by conventional methods such as chromatography and/or crystallization and can be used individually or as the mixture in subsequent steps.

Compounds of formula II may be prepared by treating a compound of formula

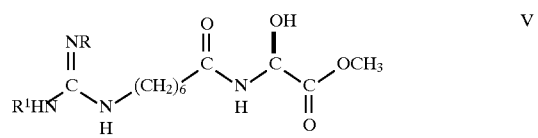

with an acylating agent such as $(XCO)_2O$ or $XC(O)Cl$ (where X is an alkyl group (such as methyl) or an aryl group (such as phenyl) in an organic solvent such as methylene chloride, toluene, tetrahydrofuran, etc., in the presence of a base such as pyridine, 1,8-diazabicyclo[5.4.0]undec-7-ene (DBU) or DIPEA, etc., to obtain a compound of formula

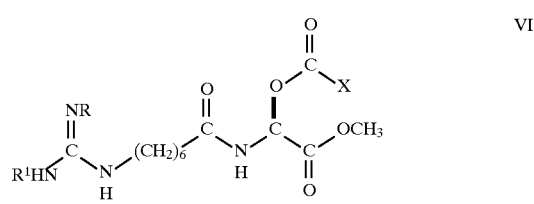

Compounds of formula VI are then reacted with an optically active benzyl alcohol such as (R)-phenethyl alcohol, (S)- phenethyl alcohol, etc., in the presence of a Lewis acid such as EtAlCl$_2$, BF$_3$OEt$_2$, MgBr$_2$, AlCl$_3$, etc., in an organic solvent such as methylene chloride, toluene, etc., to form the compounds of formula

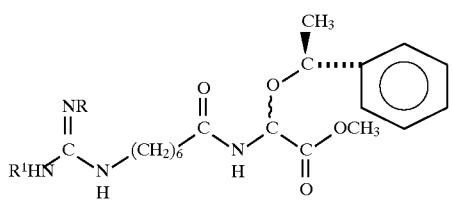
VII

Compounds of formula VII can then be hydrolyzed with bases such as LiOH, NaOH, KOH, etc., in a polar organic solvent such as tetrahydrofuran/water, water, alcohol or mixtures thereof to form the novel compounds of formula II.

Alternatively compounds of formula VII can be prepared directly by reacting a compound of formula V with an optically active benzyl alcohol such as (R)-phenethyl alcohol, (S)-phenethyl alcohol, etc., in the presence of a Lewis acid such as EtAlCl$_2$, BF$_3$OEt$_2$, MgBr$_2$, AlCl$_3$, etc., in an organic solvent such as methylene chloride, toluene, etc.

Compounds of formula VII are a mixture of two diastereomers as represented by VIIA and VIIB:

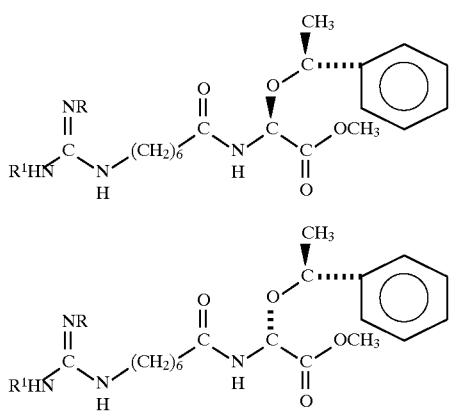

and they can be separated at this point by conventional methods such as chromatography and/or crystallization or can be used as the mixture in subsequent steps.

Compounds of formula VII (VIIA and VIIB) are novel intermediates and the reaction of compounds of formula V to form compounds of formula VII (VIIA and VIIB) is a novel process.

Compounds of formula VIIA or VIIB can also be hydrolyzed with bases such as LiOH, NaOH, KOH, etc., in a polar organic solvent such as tetrahydrofuran/water, water, alcohol or mixtures thereof to form the compounds of formula II. It should be noted that compounds of formula VIIA provide compounds of formula IIA and compounds of formula VIIB provide compounds of formula IIB.

Compounds of formula V are known and can be made by the process disclosed in *J. Org. Chem.*, 52, 1700–1703 (1987), incorporated by reference herein, or can be made by following reaction scheme A:

Scheme A

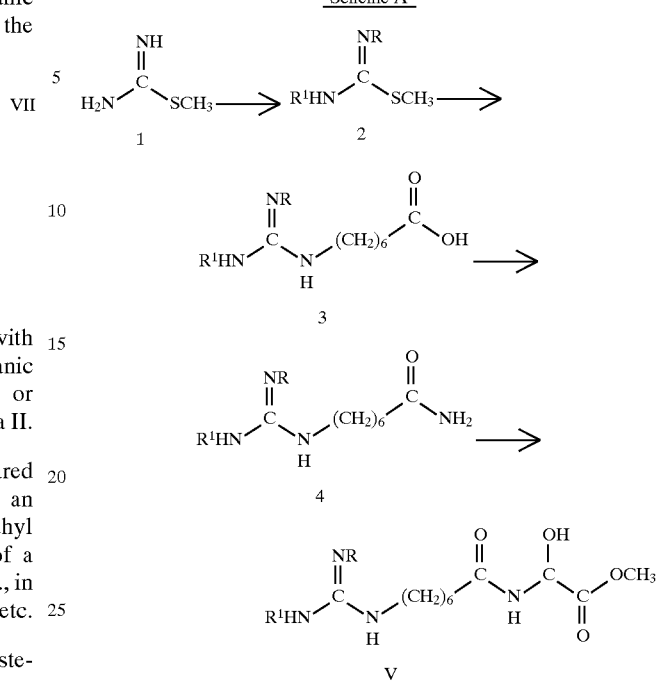

Compound (1) is reacted with a protecting group reagent such as benzyl chloroformate in a mixed solvent system such as aqueous sodium hydroxide (1N) and methylene chloride to give the di-protected product (2). Conversion of (2) to the acid derivative (3) is carried out in an organic solvent such as tetrahydrofuran and water in the presence of an organic or inorganic base such as sodium bicarbonate and 7-amino-heptanoic acid. The reaction mixture is then heated at a temperature between about 55° C. and 75° C. for about 4 to 13 hours (preferably at about 65° C. for about six hours) until the conversion is completed. The product (3) is obtained by precipitation from water. The acid derivative (3) is converted to the corresponding amide derivative (4) by a two-step procedure. The first step is to prepare an activated ester, using a coupling agent such as N-hydroxysuccinimide (NHS) or dicyclohexylcarbodiimide (DCC) in an organic solvent such as tetrahydrofuran or acetonitrile. The second step is treatment of the resulting activated ester with an amine such as methanolic ammonia solution, to yield the desired amide (4). Finally, condensation of amide (4) with a 1,2-dicarbonyl compound such as methylglyoxylate in an organic solvent such as tetrahydrofuran at a temperature between about 25° C. and 45° C. for about 2 to 30 hours (preferably at about 45° C. for about 18 hours) provides the amidol of formula V.

Compounds of formula III are known compounds and may be prepared by following the procedure in *Journal of Antibiotics.*, XLI 1629 (1988), incorporated by reference herein, or by following reaction scheme B:

Scheme B

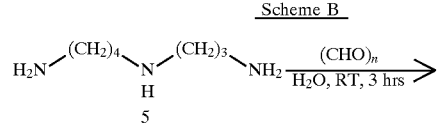

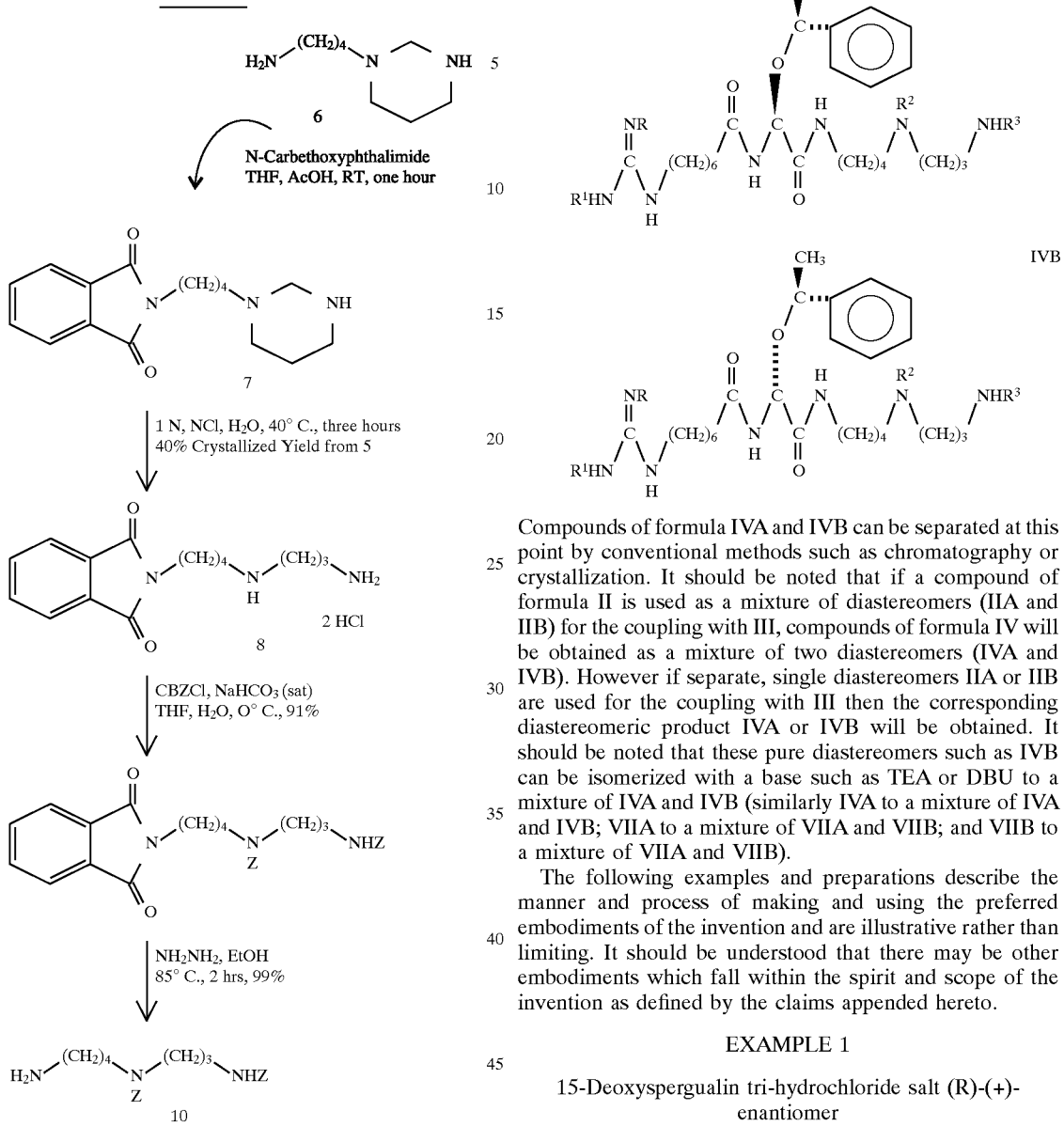

Commercially available spermidine (5) is reacted with a carbonyl compound such as formaldehyde to obtain the $N_1$, $N_4$-protected spermidine (6) which is then converted to the $N_8$ phthalimido protected spermidine (8) (through the non-isolated intermediate (7)) by reaction with N-carbethoxyphthalimide followed by acid hydrolysis. The $N_8$ phthalimido spermidine (8) is then reacted with a protecting group reagent such as benzyloxycarbonyl chloride (CBZCl) to obtain the $N_1N_4$-di-Z-$N_8$-phthalimido spermidine (9) (Z in formula (8) and (9) is benzyloxycarbonyl). Removal of the phthalimido group by hydrazenolysis provides $N_1N_4$-di-Z-spermidine (10).

Compounds of formula IV are a mixture of two diastereomers as represented by IVA and IVB:

Compounds of formula IVA and IVB can be separated at this point by conventional methods such as chromatography or crystallization. It should be noted that if a compound of formula II is used as a mixture of diastereomers (IIA and IIB) for the coupling with III, compounds of formula IV will be obtained as a mixture of two diastereomers (IVA and IVB). However if separate, single diastereomers IIA or IIB are used for the coupling with III then the corresponding diastereomeric product IVA or IVB will be obtained. It should be noted that these pure diastereomers such as IVB can be isomerized with a base such as TEA or DBU to a mixture of IVA and IVB (similarly IVA to a mixture of IVA and IVB; VIIA to a mixture of VIIA and VIIB; and VIIB to a mixture of VIIA and VIIB).

The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

15-Deoxyspergualin tri-hydrochloride salt (R)-(+)-enantiomer

A. N,N'-Bis(benzyloxycarbonyl)-S-methyl-isothiourea

Benzylchloroformate (161 mL, 1075 mmol, Aldrich, 95%) was added slowly through an addition funnel at room temperature with vigorous stirring to a solution of the sulfate salt of 2-methyl-2-thiopseudourea (74.6 g, 525 mmol) in 1N sodium hydroxide solution (1050 mL, 1050 mmol) in a 5 L three-necked round bottom flask, equipped with a 250 mL addition funnel. After the addition, stirring was continued and the reaction was monitored by TLC. The reaction was finished in ca. 20 hours. After all mono-CBZ (benzyloxy carbonyl) intermediate disappeared, the reaction mixture was transferred to a 4 L separatory funnel. The aqueous layer was separated and extracted with hexanes (1.28 L). The extracts were combined with the methylene chloride layer. The combined organic layer was washed with 553 mL of $NaH_2PO_4$ (5.7%, 533 mL, wash pH ~5) and brine (2×533 mL). It was dried over sodium sulfate, filtered and concentrated on a rotovap. The resulting residual oil was dried on a high vacuum pump to a constant weight. The remaining benzyl chloroformate, benzyl chloride and possibly benzyl alcohol were further removed by a lyophilizer. The resulting thick oil crystallized on standing in about six hours. The solid was broken up and the drying was continued to a constant weight in two days. The crude title compound thus obtained (182 g, 97% yield), was pure enough by $^1$H NMR and TLC to be used for the next reaction without any further purification.

B. 7-[N,N'-Bis(benzyloxycarbonyl)guanidino]heptanoic acid

A mixture of 7-aminoheptanoic acid (52 g, 360 mmol) and sodium bicarbonate (67.2 g, 800 mmol, 2 equiv.) in tetrahydrofuran (200 mL) and water (800 mL) was stirred vigorously and heated at a constant rate (no exotherm) to 60°–65° C. over one hour under nitrogen. A solution of the crude title A compound (144 g, 400 mmol, 1.1 equiv.) in tetrahydrofuran (600 mL) was added to the reaction mixture in a steady stream over five minutes. No exotherm was observed during the course of the addition. The heterogeneous mixture was agitated and held at 60°–65° C. to slight reflux). Slow, steady gas evolution commenced after approximately one hour, and continued through the course of the reaction. The reaction was followed by rate of gas evolution through a bubbler and by TLC. The reaction was judged complete after five hours and was cooled to ambient temperature and diluted with water (1.5 L). The reaction mixture was washed with ethyl acetate (3×500 mL). The aqueous phase (pH ~10) was separated, cooled to 0°–5° C., and cautiously acidified to pH 3 with cold (0°–5° C.) 0.85M phosphoric acid (approx. 1 L) with stirring. The product precipitated as a white solid and was collected by filtration, washed with water (2×1 L), pressed dry under a plastic cloth in vacuo over 18 hours. A total of 138.8 g of the title compound was isolated for a yield of 85% based on the amount of 7-aminoheptanoic acid used. Product identity and suitability for further transformation were confirmed by analysis and comparison of its $^1$H NMR spectrum and TLC data to a known standard.

C. 7-[N,N'-Bis(benzyloxycarbonyl)guanidino]heptanoic acid amide

Under a nitrogen atmosphere, the title B compound (169 g, 370 mmol) and 1-hydroxysuccinimide (64.5 g, 560 mmol, 1.5 equiv.) were dissolved in dimethylformamide (750 mL) and agitated at ambient temperature (approx. 20° C., no exotherm). To this solution was added 1-ethyl-3-(3-dimethylaminopropyl) carbodiimide hydrochloride (WSC, 142 g, 740 mmol, 2 equiv., also no exotherm). The reaction mixture was agitated at ambient temperature. Formation of the intermediate hydroxy succinimide ester was judged complete by TLC after approximately five hours.

The reaction mixture was cooled to 10° C. (internal temperature) and a solution of 2.0M ammonia in methanol (370 mL, 2 equiv.) was added in a steady stream over approximately five minutes. An exotherm (10°–30° C.) was observed, which subsided approximately 15 minutes after completion of the addition of the ammonia solution. The reaction mixture was stirred an additional 45 minutes at ambient temperature then checked by TLC, which showed the reaction was complete. The reaction mixture was poured into water (6 L). The product precipitated as a white solid and was filtered off and washed with water (2×1 L), dilute aqueous phosphoric acid (pH 3, 1 L); and finally water (4×1 L). The solid was pressed dry overnight in vacuo under a plastic cloth. Further drying was achieved by azeotropic distillation of a suspension of the product with toluene. The process returned a total of 164 g of the title compound for a yield of 87%. Product identity and suitability for further transformation were established by comparison of $^1$H NMR and TLC data obtained for this compound to data obtained earlier for known standards.

D. 7-[N,N'-Bis(benzyloxycarbonyl)guanidino]heptanoyl-(R,S)-2-hydroxyglycine methyl ester Under an argon atmosphere, the title C compound (164 g, 361 mmol) and methyl glyoxylate (63.5 g, 720 mmol, 2 equiv.) were suspended in tetrahydrofuran (1.2 L) and heated at a constant rate to 45° C. over 45 minutes (no exotherm). During the first hour of the reaction all solids dissolved and a pale yellow solution was obtained. The reaction was continued at 45° C. for approximately 18 hours (overnight), then analyzed by TLC which showed the reaction was complete.

The reaction mixture was cooled to ambient temperature then concentrated in vacuo to a viscous yellow oil. The oil was dissolved in ethyl acetate (250 mL), seeded with crystals from a known standard of product, and stored 18 hours (overnight) at −20° C. A first crop of product was filtered off as a white crystalline solid, washed with cold (−20° C.) ethyl acetate (200 mL) and n-hexane (50–100 mL). The product was then dried in vacuo, returning a total of 102 g of the title compound for a yield of 52%. Product identity and suitability for further transformation were established by comparison of $^1$H NMR and TLC data on the product to known standards.

E. 7-[N,N'-Bis(benzyloxycarbonyl)guanidino]heptanoyl-(R,S)-2-(R-sec-phenethoxy)glycine methyl ester The title D compound (100 g, 171 mmol) was dissolved in methylene chloride (newly opened bottle, 2 L) in a 5 L three-necked round bottom flask, equipped with a mechanical stirrer, an argon line and a 250 mL addition funnel. The solution was cooled to 0° C. (internal) with an ice bath. Anhydrous pyridine (225 mL, 2,986 mmol) was added dropwise through the addition funnel. The internal temperature remained below 3° C. during the course of the addition. Neat acetic anhydride (130 mL, 1,493 mmol) was added in the same manner. The resulting reaction mixture was warmed to room temperature and stirred for one hour. The reaction was complete as indicated by TLC. The yellowish reaction mixture was cooled to 5° C. and quenched with dropwise addition of anhydrous methanol (55 mL, 1,453 mmol). After 15 minutes of stirring at 5° C., the reaction mixture was evaporated to an oily residue. Anhydrous toluene (500 mL) was added to the residue and concentrated on a rotovap. The addition and removal of anhydrous toluene were repeated three more times until TLC and $^1$H NMR showed the residue did not contain any pyridine.

The resulting yellowish oil was re-dissolved in methylene chloride (2 L). The solution was cooled to −78° C. and EtAlCl$_2$ (460.8 mL, 1.0M in hexane, 460.8 mmol) was added dropwise through an addition funnel under argon. After ten minutes of stirring, a mixture of neat R-phenethyl alcohol (33.2 mL, 276.4 mmol) and diisopropylethylamine (48.2 mL, 276.4 mmol) was added in the same manner. The reaction mixture was warmed to room temperature and stirred for 16 hours. The reaction was complete as indicated by TLC. It was cooled to −78° C. and quenched with slow addition of a saturated aqueous solution of potassium sodium tartarate (100 mL) and then potassium sodium tartarate solid (100 g). The mixture was warmed up to 0° C. and stirred for three hours. The cold mixture was filtered through a pad of celite. The filtrate was washed with Rochelle salt solution (3×500 mL), dried over sodium sulfate and concentrated to give 150 g of crude oil, which was passed through a pad of silica gel (300 g, 23–40 μm), eluted with 33–50% ethyl acetate in hexanes. The solvents were evaporated to give 104 g of spectroscopically pure methyl ester title compound as a thick oil in 74% yield.

F. 7-[N,N'-Bis(benzyloxycarbonyl)guanidino]heptanoyl-(R,S)-2-(R-sec-phenethoxy)glycine To a solution of the title E compound (88 g, 136 mmol) in tetrahydrofuran (3 L) in a 5 L three-necked round bottom flask, equipped with a mechanical stirrer, and an addition funnel was added dropwise lithium hydroxide (0.2M, 843 mL). After stirring at room temperature for one hour, the reaction was complete as indicated by TLC. The tetrahydrofuran was evaporated (bath T <40° C.) and the aqueous layer was diluted with ethyl acetate (1 L) and phosphoric acid (0.2M, 850 mL). The aqueous layer was separated and extracted with ethyl acetate (2×200 mL). The organic layers were combined, washed with brine (2×500 mL), dried over sodium sulfate, filtered and concentrated to give 80 g of spectroscopically pure acid title compound as a thick oil in 93% yield.

G. $N_1,N_4$-Bis(benzyloxycarbonyl)spermidine

To a suspension of $N_1N_4$-di-Z-$N_8$-phthalimido spermidine (10-N-phthaloyil-1,5-di-Z-1,5,10-triazadecane; 60 g, 110.1 mmol) in ethanol (120 mL) in a 200 mL round bottom flask equipped with a condenser under argon was added hydrazine (12.1 mL, 385.3 mmol). The mixture was heated at 75° C. for three hours. The reaction was complete as indicated by TLC. A white solid formed at the end of the reaction. The solid was removed by filtration at room temperature and washed with toluene (4×100 mL). Additional filtrations were carried out to remove the remaining solid in the filtrate. The filtrate was evaporated. The oily residue was dissolved in toluene (800 mL). The remaining solid was removed by filtration and washed with toluene (2×100 mL). The filtrate was transferred to a 4 L separatory funnel, diluted to 500 mL with ethyl acetate, and washed with brine (3×500 mL). It was dried over sodium sulfate, filtered and concentrated to give a colorless thick oil. A constant weight of 49 g was obtained after azeotropic evaporation with toluene (3×200 mL) and three hours of high vacuum drying.

H. Tetra-CBZ-(R,S)-11-(R-sec-phenethoxy)-15-deoxyspergualin

The title F compound (70 g, 110.6 mmol) and the title G compound (49 g, 118.6 mmol) were dissolved in methylene chloride (750 mL) in a 2 L three-necked round bottom flask, equipped with a mechanical stirrer. The solution was cooled to –5° C. Triethylamine (30.8 mL, 221.0 mmol) was added through a syringe, followed by the dropwise addition of PPA (105.52 g, 50% ethyl acetate solution, 165.8 mmol). The reaction was stirred at –5° C. for one hour. It was then diluted with ethyl acetate (500 mL) and quenched with the addition of a few chunks of ice. The mixture was transferred to a 4 L separatory funnel and was further diluted with ethyl acetate (1.5 L). The organic layer was separated and washed with $NaH_2PO_4$ (5.7% in brine, 3×800 mL). It was dried over sodium sulfate, evaporated to 500 mL, filtered through a pad of silica gel (23–40 μm, 500 g), washed with 50–75% of ethyl acetate in hexanes. The filtrate was concentrated to give 115 g of a mixture of two diastereoisomers, as a thick crude oil.

I. Tetra-CBZ-R-11-(R-sec-phenethoxy)-15-deoxyspergualin

The crude diastereomeric mixture of the diastereoisomers of the title H compound (233 g total) was separated in four days by normal phase HPLC to give 92 g of the title diastereoisomer as a thick oil and 118 g of second diastereoisomer (tetra-CBZ-S-11-(R-sec-phenethoxy)-15-deoxyspergualin) as a white solid. Ethyl acetate (65 gallons) and hexanes (10 gallons) were used and 15 injections were carried out to load 223 g of the mixture. Eleven more injections were made to separate the contaminated mixed fractions.

J. (R)-(+)-15-Deoxyspergualin

The title I compound (91 g, 88.6 mmol) was dissolved in methanol (2 L) and acetic acid (0.2 L). The resulting solution was added to a 5 L three-necked round bottom flask, equipped with an air driven mechanical stirrer, a hydrogen/argon inlet line and an outlet line connected to a trap, house vacuum, and oil bubbler and a balloon. The flask was charged with palladium on charcoal (5%, 28 g), palladium on charcoal (10%, 14 g) and $Pd(OH)_2/C$ (20%, 36 g) mixed with methanol (1 L) and acetic acid (0.1 L). The heterogeneous solution was stirred at room temperature for 20 hours under hydrogen balloon pressure. The reaction was 90–95% complete by NMR. More palladium on charcoal (10%, 20 g, wet) and $Pd(OH)_2/C$ (20%, 5 g, wet) were added through a powder funnel to the reaction mixture. The stirring was continued for ten more hours. The catalysts were then filtered off on a celite pad and washed with 4×750 mL water. The water/methanol/acetic acid solution was stripped to 3 L at room temperature. The resulting aqueous layer was washed with methylene chloride (3×1 L). It was slightly evaporated and then lyophilized in two 5 L round bottom flasks to give 42 g (HI 93.5%) of crude (R)-(+)-15-deoxyspergualin tri-acetate, which was further purified by chromatography over CM Sephadex C-25 and Sephadex LH-20 columns to give methanolic solution of pure title compound. The tri-acetate salt was converted to the corresponding tri-hydrochloride salt on the CM sephadex C-25 column by sodium chloride.

K. 15-Deoxyspergualin tri-hydrochloride salt (R)-(+)-enantiomer

The title J compound was evaporated on a rotovap and then dried on high vacuum to give the title compound as a white solid in two batches (20 g and 13 g).

EXAMPLE 2

15-Deoxyspergualin tri-hydrochloride salt (S)-(–)-enantiomer

The "second diastereoisomer" (tetra-CBZ-(S)-11-(R-sec-phenethoxy)-15-deoxyspergualin) (65 g, 63.3 mmol; prepared as described in the section for the title I compound of Example 1) was dissolved in methanol (1.73 L) and acetic acid (173 mL). The resulting solution was added to a 5 L three-necked round bottom flask, equipped with an air driven mechanical stirrer, a hydrogen/argon inlet line and an outlet line connected to a trap, house vacuum, an oil bubbler and a balloon. The flask was charged with palladium on charcoal (5%, 39 g) and $Pd(OH)_2/C$ (20%, 26 g) mixed with methanol (870 mL) and acetic acid (87 mL). The heterogeneous solution was stirred at room temperature for 20 hours under hydrogen balloon pressure. The reaction was complete as indicated by NMR. The catalysts were then filtered off on a celite pad and washed with water (4×500 mL). The water/methanol/acetic acid solution was concentrated to 2 L at room temperature. The resulting aqueous layer was washed with methylene chloride (3×800 mL). It was slightly evaporated and lyophilized in two 5 L round bottom flasks to give 36 g (HI 84%) of crude (S)-(–)-15-deoxyspergualin tri-acetate, which was combined with 15 g of material form a 30 g input and further purified by chromatography over CM Sephadex C-25 and Sephadex LH-20 columns to give methanolic solution of pure title compound. It was evaporated on a rotovap and then dried on high vacuum to give the tri-hydrochloride salt of the title compound as a white solid in three batches (20 g, 10 g and 3 g).

EXAMPLE 3

7-[N,N'-Bis(benzyloxycarbonyl)guanidino]-heptanoyl-(S)-2-(R-sec-phenethoxy)glycine The title F compound of Example 1 (10 g, 1:1 mixture of diastereomers) was dissolved in toluene (65 mL) at 40° C. and set aside at room temperature overnight. The crystals were filtered, washed with toluene (10 mL) and suction dried to get 4 g of the title compound (diastereomer A) as a white solid. HPLC and TLC analysis indicated it is 96:4 mixture of the title compound and the other diastereomer (B), respectively.

Evaporation of the other liquor (filtrate) and washings gave 6 g of the diastereomer B as a thick oil. HPLC and TLC analysis indicated that it is a mixture of diastereomers in a ratio of 17:83 (A:B).

Re-crystallization of the title compound of Example 3

7-[N,N'-Bis(benzyloxycarbonyl)guanidino]-heptanoyl-(S)-2-(R-sec-phenethoxy)glycine (1 g, mixture of diastereomers A:B, 96:4) was dissolved in toluene (4 mL) and the crystals were filtered to give 95% yield with 98.5:1.5 ratio (A:B diastereomers). Recrystallization from 8 mL of toluene (1 g in 8 mL) gave 74% yield with 99.9:01 ratio of A:B.

EXAMPLE 4

Tetra-CBZ-(S)-11-(R-sec-phenethoxy)-15-deoxyspergualin

The title compound of Example 3 (0.29 g, 0.46 mmol) and the title G compound of Example 1 (0.39 g, 0.92 mmol) were dissolved in methylene chloride (3 mL) in a 25 mL three-necked round bottom flask, equipped with a mechanical stirrer. The solution was cooled to −5° C. Triethylamine (128 μL, 0.92 mmol) was added through a syringe, followed by the dropwise addition of PPA (0.22 g, 50% ethyl acetate solution, 0.69 mmol). The reaction was stirred at −5° C. for one hour. It was then diluted with ethyl acetate (50 mL) and quenched with the addition of a few chunks of ice. The mixture was transferred to a 100 mL separatory funnel. The organic layer was separated and washed with $NaH_2PO_4$ (5.7% in brine, 3×20 mL). It was dried over sodium sulfate, evaporated to give 0.4 g of the title compound (diastereomer A). HPLC analysis indicated it was a mixture of diastereomers in 95:5 (A:B) ratio. The starting material, the title compound of Example 3 was a mixture of diastereomers in a ratio of 95:5 (A:B).

EXAMPLE 5

10-N-Phthaloyil-1,5-di-Z-1,5,10-triazadecane

A. 1-(4-Aminobutyryl)hexahydropyrmidine

To a solution of 7.5 g of spermidine in water (150 mL) in a 250 mL round bottom flask was added paraformaldehyde (1.6 g). The resulting solution was stirred at room temperature for three hours. TLC (silicon dioxide, ethyl acetate-:methanol:ammonium hydroxide=3:6:1) indicated there was no S.M. (Rf-0.01). To the reaction mixture was added toluene (100 mL). The resulting heterogeneous solution was concentrated on a rotovap at 45° C. for 30 minutes. The addition of toluene (100 mL) and concentration at 45° C. was repeated for two more times. The resulting thick oil was washed with tetrahydrofuran:ethanol (10:1)(×3) (220 mL). The combined organic layers were dried with sodium sulfate, filtered and concentrated to give 8.64 g of the title compound as a crude thick oil (yield 103%).

B. 1-(4-Phthalimido butyryl)hexahydropyrmidine

Crude title A compound (8.64 g) was dissolved in tetrahydrofuran (50 mL) in a 250 mL round bottom flask. To the resulting solution was added dropwise with stirring N-carbethoxyphthalimide (12.04 g) in tetrahydrofuran (20 mL) at 0° C. TLC (silica gel, ethyl acetate:methanol:ammonium hydroxide=3:6:1) indicated that the S.M. (Rf=0.1) almost disappeared. Acetic acid (14 mL) was added and the reaction mixture was stirred at room temperature for one hour. Tetrahydrofuran was removed on a rotovap at 40° C. to provide the title compound (which was not isolated).

C. 10-N-Phthaloyil-1,5,10-triazadecane

The residue from step B was dissolved in water (30 mL). Hydrochloric acid (1N, 70 mL) was added to the aqueous solution (pH=1–2). The mixture was washed with ethyl acetate (100 mL). The clear aqueous solution was concentrated on a rotovap at 50° C. with addition of ethanol:toluene (1:1) (×3) (40 mL) to give 20 g of a yellowish solid, which was dissolved in ethanol:water (95:5) (170 mL) at 85° C. The clear solution was cooled down and was seeded at 38° C. Crystallization occurred after a few minutes. The mixture was put aside at room temperature for four hours then in a −10° C. freezer overnight. It was filtered and the residue was washed with cold ethanol (×2) (15 mL) to give 7.0 g of the title compound as a white solid (total yield 40%).

D. 10-N-Phthaloyil-1,5-di-Z-1,5,10-triazadecane

Into a 500 mL round bottom flask containing 6.4 g of the title C compound was added saturated sodium bicarbonate solution (109 mL). The resulting solution was stirred at room temperature for 15 minutes and then dioxane (64 mL) was added. The resulting milk-like mixture was cooled down to 0° C. and benzyloxycarbonyl chloride (7.7 mL) was added dropwise. The reaction mixture was allowed to warm to 15° C. and then cooled back down to 0° C. and stirred for a total of three hours. TLC (silica gel, ethyl acetate:hexanes=6:4, product $R_f$=0.4) indicated the reaction was complete. The mixture was diluted with ethyl acetate (320 mL) and washed with saturated $NaHCO_2$ (×2)(200 mL) and brine (×2)(200 mL). The organic layer was dried with sodium sulfate, filtered and concentrated on a rotovap. The residue was put on a high vacuum pump overnight to give 12.6 g of the title compound as a thick oil, which was crystallized as follows. The crude title D compound (4.8 g) was dissolved in hot ethanol (5 mL). The resulting solution was cooled to room temperature and then water (1 mL) was added dropwise so that the solution became cloudy. About five drops of ethanol was added back. The solution was seeded at room temperature and become cloudy immediately. Four more drops of ethanol was added and the mixture was put aside at room temperature for three hours and then at 4° C. for 16 hours. The mixture was filtered and the filtrate was washed with cold ethanol (×4) (3 mL) to give 3.6 g of the title compound as a white solid.

What is claimed is:

1. The compounds of formula

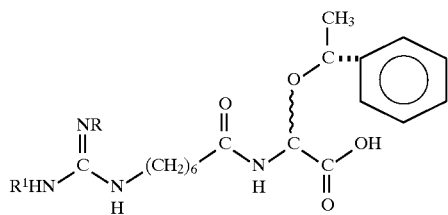

where R and R$^1$ are nitrogen protecting groups.

2. The compounds as recited in claim 1 wherein the nitrogen protecting groups are benzyloxycarbonyl or t-butoxycarbonyl.

3. The compounds as recited in claim 1 having the structure

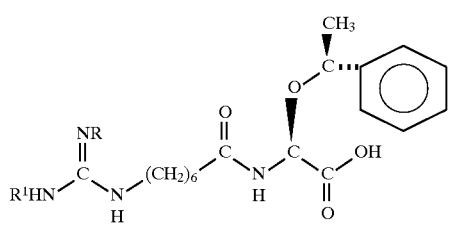

4. The compounds as recited in claim 1 having the structure

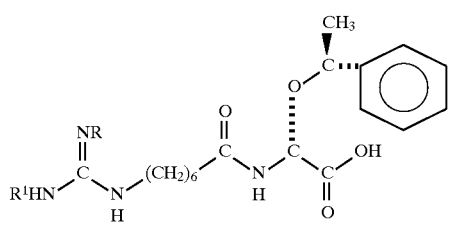

5. The compounds of formula

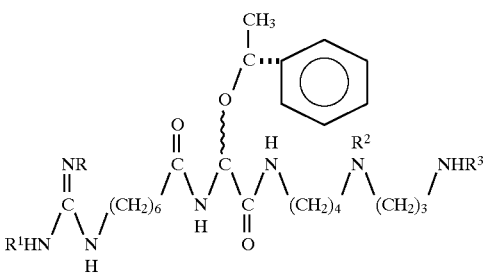

where R$^2$ and R$^3$ are nitrogen protecting groups.

6. The compounds as recited in claim 5 wherein the nitrogen protecting groups are benzyloxycarbonyl or t-butoxycarbonyl.

7. The compounds of formula

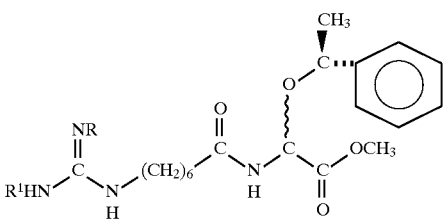

where R and R$^1$ are nitrogen protecting groups.

8. The compounds as recited in claim 7 where the nitrogen protecting groups are benzyloxycarbonyl or t-butoxycarbonyl.

* * * * *